United States Patent [19]

Takahashi et al.

[11] Patent Number: 4,925,843

[45] Date of Patent: May 15, 1990

[54] 2-PYRIDYLMETHYLTHIO DERIVATIVES AS ANTIULCER AGENTS

[75] Inventors: Toshihiro Takahashi; Koichiro Hagihara; Koichi Nakamaru; Yoshikuni Suzuki, all of Saitama, Japan

[73] Assignee: Nisshin Flour Milling Co., Ltd., Tokyo, Japan

[21] Appl. No.: 331,513

[22] Filed: Mar. 29, 1989

[30] Foreign Application Priority Data

Apr. 11, 1988 [JP] Japan .................. 63-87271

[51] Int. Cl.$^5$ ............... C07D 401/12; C07D 401/14; A61K 31/50; A61K 31/505
[52] U.S. Cl. ...................... 514/248; 514/258; 514/259; 544/237; 544/279; 544/284
[58] Field of Search .............. 544/237, 279, 284; 514/248, 258, 259

[56] References Cited

U.S. PATENT DOCUMENTS 4,738,970  4/1988  Uchida .................. 514/303

FOREIGN PATENT DOCUMENTS 62-209062  9/1987  Japan .

*Primary Examiner*—Mark L. Berch
*Attorney, Agent, or Firm*—Abelman Frayne Rezac & Schwab

[57] ABSTRACT

2-Pyridylmethylthio derivatives of formula (I) are provided.

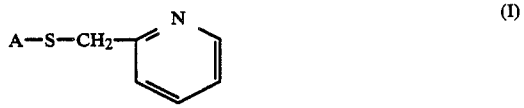

(I)

wherein A represents 4-methyl-2-quinazolinyl, 4-(2-pyridylmethylthio)-1-phthalazinyl or 4-oxo-3-phenyl-3,4-dihydropyrido[2,3-d]pyrimidine-2-yl, or a pharmaceutically acceptable acid addition salt thereof. They are useful as antiulcer agents.

8 Claims, No Drawings

2-PYRIDYLMETHYLTHIO DERIVATIVES AS ANTIULCER AGENTS

FIELD OF THE INVENTION

This invention relates to new 2-pyridylmethylthio derivatives and pharmaceutically acceptable salts thereof, having prominent antiulcer activity.

BACKGROUND OF THE INVENTION

The agents used as the antiulcer drugs include $H_2$-receptor antagonists, anticholinergic agents, gastric mucosal protective agents and antacids, which are used depending upon the symptom of patients. These known agents, however, are of such drawbacks as generally weak activity and frequent occurrence of side effects.

For example, cimetidine, which is a $H_2$-receptor antagonist widely employed, is known to have side effects such as gynecomastism. Moreover, numbers of cases are reported about recurrence of ulcer after suspension of administration with cimetidine. Anticholinergic agents are known to have such side effects as suppression of gastric motility, corediastasis and thirst. Furthermore, they exhibit activity only for a limited period of time. Antacids are known to have frequent occurrence of such side effects as constipation.

As described above, known antiulcer agents were limitedly used in terms of manner of administration due to their side effects, and they have common drawback of exhibiting somewhat weak activity.

Japanese Patent LOP Publication No. 209062/87 discloses 2-pyridylmethylthio (or sulfinyl) substituted-condensed ring compounds which are useful as the medicine for the prevention and treatment of stomach disorder. In this publication, however, no specific pharmacological data is given on the antiulcer activity.

The present invention results from efforts to develop new quinoxaline derivatives with more improved antiulcer activity.

DISCLOSURE OF THE INVENTION

According to the invention, there are provided 2-pyridylmethylthio compounds of formula (I)

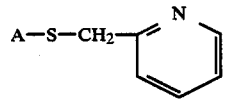
(I)

wherein A represents 4-methyl-2-quinazolinyl, 4-(2-pyridylmethylthio)-1-phthalazinyl or 4-oxo-3-phenyl-3,4-dihydropyrido[2,3-d]pyrimidine-2-yl, and pharmaceutically acceptable acid addition salts thereof.

The compounds of formula (I) are generally prepared by reacting a mercaptide of formula (II)

    (II)

wherein A has the same meaning as defined above, with a compound of formula (III)

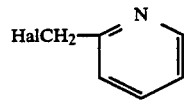   (III)

wherein Hal represents a halogen atom in the presence of a base. In the reaction, the compound of formula (III) is used in the proportion of 0.5 to 5 moles per mole of the compound (II).

The reaction can be conducted at temperatures of 0° C. to 150° C. in an aqueous medium or an organic solvent. The organic solvents include for example lower alcohols such as methanol, ethanol or propanol; ethers such as diethyl ether or tetrahydrofuran; esters such as ethyl acetate or butyl acetate; ketones such as acetone or ethyl methyl ketone and halogenated hydrocarbons.

The compounds of formula (III) used in the reaction include those wherein halogen is chlorine, bromine or iodine, but the preferred compounds are those wherein halogen is chlorine because of their easy availability. The bases used in the reaction include inorganic bases such as sodium hydroxide, potassium hydroxide or ammonium hydroxide, organic bases such as diethylamine, triethylamine or pyridine, and alkali metal alkoxides such as sodium methoxide, potassium methoxide, sodium ethoxide or potassium t-butoxide.

Concrete examples of the compounds of formula (II) used as one starting material in the reaction include 2-mercapto-4-methyl-quinazoline, 1,4-dimercaptophthalazine and 2-mercapto-4-oxo-3-phenyl-3,4-dihydropyrido[2,3-d]pyrimidine.

Concrete examples of the compounds of formula (III) used as the other starting material include 2-chloromethylpyridine, 2-bromomethylpyridine and 2-iodomethylpyridine.

Illustrative of the compounds of formula (I) are 4-methyl-2-(2-pyridylmethylthio)-quinazoline, 1,4-di(2-pyridylmethylthio)-phthalazine, 4-oxo-3-phenyl-2(2-pyridylmethylthio)-3,4-dihydropyrido[2,3-d]pyrimidine.

The compounds of formula (I) can be converted, if desired, to pharmaceutically acceptable acid addition salts thereof which are included within the scope of the present invention.

Illustrative of addition salts are the salts of the compounds with inorganic acids such as hydrochloric acid, hydrobromic acid, hydroiodic acid, nitric acid, sulfuric acid or phosphoric acid, and organic acids such as formic acid, acetic acid, propionic acid, butyric acid, maleic acid, fumaric acid, malonic acid, succinic acid, malic acid, citric acid, tartaric acid or oxalic acid.

The compounds of formula (I) and pharmaceutically acceptable acid addition salts thereof are of prominent antiulcer activity.

Thus, the present invention also provides antiulcer agents which comprise as an active ingredient the compounds of formula (I) or pharmaceutically acceptable acid addition salts thereof, optionally in admixture with additives for pharmaceutical preparation.

The pharmaceutical compositions of the invention may be formulated into various forms which are commonly used in the art and which are administered orally or parenterally. For example, they may be formulated into tablets, capsules, suppositories, troches, syrups, creams, ointments, granules, powders, injectable solutions or suspensions. Alternatively, they may be formulated into double or multiple layer tablets, together with other active principles. Furthermore, they may be formulated into coated tablets such as sugar-coated tablets, enteric-coated tablets and film-coated tablets.

In order to obtain solid preparations, the compounds of this invention are mixed with such conventional diluents or fillers as lactose, refined sugar, crystalline cellulose, corn starch, calcium phosphate, sorbitol, glycine, carboxymethyl cellulose, gum arabic, polyvinylpyrrolidone, hydroxypropyl cellulose, glycerol, polyethylene glycol, stearic acid, magnesium stearate or talc.

In order to obtain semi-solid preparations, the compounds of this invention are mixed with such additives as plant wax, synthetic wax or fats.

In order to obtain liquid preparations, the compounds of this invention are mixed with such diluents or additives as sodium chloride, sorbitol, glycerol, olive oil, almond oil, propylene glycol or ethanol.

The compounds of the invention may normally be contained in a preparation in an amount of from 0.1 to 100% by weight, more suitably in an amount of from 1 to 50% by weight in the case of preparations for oral administration and from 0.2 to 20% by weight in the case of injectable preparations.

There is no particular limitation as to the method of administration and the dosage of the antiulcer agents according to the invention. They are chosen, depending on the form of preparation, age of patients, sex, degree of symptom, etc. Normally, however, the dosage will be in the range of from 10 to 1,000 mg per day.

The pharmaceutical composition of the invention may be administered in conjunction with one or more other active principles such as antacids, non-steroid anti-inflammatory agents or other types of antiulcer agents.

The invention is further illustrated by the following examples which are not to be construed to limit the scope thereof.

EXAMPLE 1

Preparation of
4-methyl-2-(2-pyridylmethylthio)quinazoline 22.3 ml of 28% methanolic solution of sodium methoxide were added to a solution of 9.71 g of 2-mercapto-4-methyl-quinazoline and 9.0 g of 2-chloromethylpyridine hydrochloride in 100 ml of methanol and stirred at room temperature for 3 hours.

The reaction solution was poured into 200 ml of water and extracted with chloroform.

The chloroform layer was dried over sodium sulfate and evaporated under reduced pressure. The residue was purified by silica gel column chromatography eluting with 20% acetone/chloroform to give 6.55 g of the title compound.

Yellow crystals (from isopropyl ether)
mp 74.9°–78.5° C.
NMR (CDCl$_3$): 2.86(3H,s), 4.70(2H,s), 7.10–7.18(1H,m), 7.42–7.64(3H,m), 7.72–7.89(2H,m), 7.99(1H,d,8 Hz), 8.56(1H,d,5 Hz)
IR (nujol): 1615, 1580
MASS: 267(M+), 234

EXAMPLE 2

Preparation of 1,4-di(2-pyridylmethylthio)-phthalazine 23 ml of 28% methanolic solution of sodium methoxide were added to a solution of 5.77 g of 1,4-dimercaptophthalazine and 9.2 g of 2-chloromethylpyridine hydrochloride in 100 ml of methanol and stirred at room temperature for 4 hours. The reaction solution was poured into 200 ml of water and extracted with chloroform. The chloroform layer was dried over sodium sulfate and evaporated under reduced pressure. The residue was purified by silica gel column chromatography eluting with 50% ethyl acetate/chloroform to give 4.12 g of the title compound.

White crystals (from ethyl acetate)
mp 183.2°–186.8° C.
NMR (CDCl$_3$): 4.91(4H,s), 7.15–7.25(2H,m), 7.52–7.71(4H,m), 7.76–7.89(2H,m), 8.05–8.16(2H,m), 8.61(2H,d,5 Hz)
IR (nujol): 1590

EXAMPLE 3

Preparation of
4-oxo-3-phenyl-2-(2-pyridylmethylthio)-3,4-dihydropyrido[2,3-d]pyrimidine 2.0 ml of 28% methanolic solution of sodium methoxide were added to a solution of 1.18 g of 2-mercapto-4-oxo-3-phenyl-3,4-dihydropyrido[2,3-d]pyrimidine and 0.83 g of 2chloromethylpyridine hydrochloride in 50 ml of methanol and stirred at room temperature for 3 hours. The crystals precipitated in the reaction solution were collected by filtration to give 1.02 g of the title compound.

White crystals
mp 230.6°–233.1° C.
NMR (CDCl$_3$): 4.72(2H,s), 7.13–7.23(1H,m), 7.27–7.74(8H,m), 8.52(1H,d,5 Hz), 8.58(1H,d,8 Hz), 8.96(1H,d,5 Hz)

EXAMPLE 4

This example illustrates the determination for the antiulcer activity of the compounds according to the invention.

Four-week-old ddY series male mice were used as the test animals after they were fasted for 24 hours. Each test compound suspended in a 1% gum arabic solution was administered to the stomach of each mouse at a dose of 100 mg/kg, and then, after 30 minutes, 20 mg/kg of indomethacin was administered orally. Four hours after the administration of indomethacin, the stomach of mouse was extirpated and the length of ulcers was measured. Then, the ulcer index was determined by the total sum of the scores as calculated in Table 1.

TABLE 1

| Length of ulcer | 0.5 mm< | 1 mm< | 2 mm< | 3 mm< |
|---|---|---|---|---|
| Score | 0.5 | 1 | 2 | 3 |

The mean ulcer index of each group was calculated and the suppression rate against the control group in terms of difference in the mean ulcer index was determined. The results are shown in Table 2.

TABLE 2

| Compound tested | Suppression rate of indomethacin induced ulcer, 100 mg/kg, p.o. |
|---|---|
| 4-Methyl-2-(2-pyridylmethylthio)-quinazoline | 54 |
| 1,4-Di(2-pyridylmethylthio)-phthalazine | 79 |
| 4-Oxo-3-phenyl-2-(2-pyridylmethylthio)-3,4-dihydropyrido[2,3-d]pyrimidine | 68 |

Table 2 shows that the compounds of the invention possess prominent antiulcer activity.

The following examples illustrate the various types of preparations which comprise as an active ingredient the compounds of the invention.

Preparation 1  Tablet 50 mg of 1,4-di(2-pyridylmethylthio)-phthalazine, 77 mg of lactose, 15 mg of crystalline cellulose, 7 mg of corn starch and 1 mg of magnesium stearate (each per tablet) were thoroughly mixed, and then the mixture was tableted with a rotary tableting machine into a tablet of 7 mm diameter, weight 150 mg.

Preparation 2  Granule 50 mg of 4-oxo-3-phenyl-2-(2-pyridylmethylthio)-3,4-dihydropyrido[2,3-d]pyrimidine, 230 mg of lactose, 110 mg of corn starch and 100 mg of crystalline cellulose were thoroughly mixed. Meanwhile, 10 mg of hydroxypropyl cellulose were dissolved in 90 mg of ethanol and the solution was added to the previously prepared mixture. The whole mixture was kneaded and granulated. The granules were air-dried at 50° C. and then sieved into the grain size of from 297 μm to 1460 μm. 500 mg of the granules were packed into a unit dosage form.

Preparation 3  Syrup 5 g of 4-methyl-2-(2-pyridylmethylthio)-quinazoline, 30 g of refined sugar, 25 g of 70 w/v % D-sorbitol, 0.03 g of ethyl p-hydroxybenzoate and 0.015 g of propyl p-hydroxybenzoate were dissolved in 60 ml of warmed water. After the solution was cooled, a solution of 0.2 g of a flavor in 0.15 g of glycerol and 0.5 g of 96% ethanol was added. The whole mixture was diluted with water to balance 100 ml.

Preparation 4  Injectable solution 5 mg of 1,4-di(2-pyridylmethylthio)-phthalazine and 10 mg of sodium chloride were dissolved in sterilized distilled water to balance 1 ml.

Preparation 5  Suppository 20 g of polyethylene glycol 4000 were added to a solution of 10 g of 1,4-di(2-pyridylmethylthio)-phthalazine in 70 g of glycerol. The mixture was warmed and poured into a suppository mold and then cooled to give suppositories, each weighing 1.5 g.

What is claimed is:

1. A compound of formula (I)

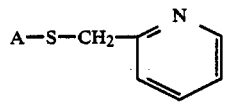

(I)

wherein A represents 4-methyl-2-quinazolinyl, 4-(2-pyridylmethylthio)-1-phthalazinyl or 4-oxo-3-phenyl-3,4-dihydropyrido[2,3-d]pyrimidine-2-yl, or a pharmaceutically acceptable acid addition salt thereof.

2. A compound of claim 1 wherein A is 4-methyl-2-quinazolinyl.

3. A compound of claim 1 wherein A is 4-(2-pyridylmethylthio)-1-phthalazinyl.

4. A compound of claim 1 wherein A is 4-oxo-3-phenyl-3,4-dihydropyrido[2,3-d]pyrimidine-2-yl.

5. An antiulcer agent which comprises as an active ingredient a therapeutically effective amount of a compound of formula (I)

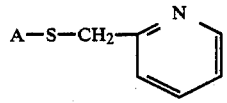

(I)

wherein A represents 4-methyl-2-quinazolinyl, 4-(2-pyridylmethylthio)-1-phthalazinyl or 4-oxo-3-phenyl-3,4-dihydropyrido[2,3-d]pyrimidine-2-yl, or a pharmaceutically acceptable acid addition salt thereof) in a pharmaceutically acceptable carrier.

6. An antiulcer agent of claim 5 wherein the active ingredient is a compound of formula (I) wherein A is 4-methyl-2-quinazolinyl.

7. An antiulcer agent of claim 5 wherein the active ingredient is a compound of formula (I) wherein A is 4-(2-pyridylmethylthio)-1-phthalazinyl.

8. An antiulcer agent of claim 5 wherein the active ingredient is a compound of formula (I) wherein A is 4-oxo-3-phenyl-3,4-dihydropyrido[2,3-d]pyrimidine-2-yl.

* * * * *